(12) United States Patent
Guthrie et al.

(10) Patent No.: US 8,994,395 B2
(45) Date of Patent: Mar. 31, 2015

(54) METHODS AND DEVICES FOR MITIGATING ESD EVENTS

(75) Inventors: Brian Guthrie, Inverness (GB); Allan Macrae, Inverness (GB); Keith Lawrie, Inverness (GB); Allan Faulkner, Inverness (GB); Chin Wee Lee, Singapore (SG); Jia Yian Tan, Alameda, CA (US)

(73) Assignee: LifeScan Scotland Limited, Inverness (GB)

( * ) Notice: Subject to any disclaimer, the term of this patent is extended or adjusted under 35 U.S.C. 154(b) by 868 days.

(21) Appl. No.: 13/126,445

(22) PCT Filed: Oct. 21, 2009

(86) PCT No.: PCT/GB2009/002502
§ 371 (c)(1),
(2), (4) Date: Apr. 27, 2011

(87) PCT Pub. No.: WO2010/049669
PCT Pub. Date: May 6, 2010

(65) Prior Publication Data
US 2011/0210951 A1    Sep. 1, 2011

Related U.S. Application Data

(60) Provisional application No. 61/108,839, filed on Oct. 27, 2008.

(51) Int. Cl.
G01R 31/26 (2014.01)
G09G 3/36 (2006.01)

(52) U.S. Cl.
CPC .......... *G09G 3/3611* (2013.01); *G09G 2330/08* (2013.01)
USPC .................................................... 324/760.01

(58) Field of Classification Search
CPC .... G09G 3/006; G09G 3/3611; G09G 3/3648
USPC ................................ 324/760.01; 345/87, 204
See application file for complete search history.

(56) References Cited

U.S. PATENT DOCUMENTS

| 4,043,112 A | 8/1977 | Tanaka |
| 4,677,428 A | 6/1987 | Bartholow |
| 4,750,040 A | 6/1988 | Hakamada |
| 5,046,029 A | 9/1991 | Ikeda |
| 5,390,322 A | 2/1995 | O'Brian et al. |
| 5,708,247 A | 1/1998 | McAleer et al. |

(Continued)

FOREIGN PATENT DOCUMENTS

| CN | 1413049 A | 4/2003 |
| CN | 100407278 C | 7/2008 |

(Continued)

OTHER PUBLICATIONS

Japanese Patent Application No. 2011-533806, Japanese Notice of Reasons for Rejection dated Jun. 4, 2013, 2 pages, Japanese Patent Office.

(Continued)

*Primary Examiner* — Tung X Nguyen (57) ABSTRACT

Various embodiments are described and illustrated for mitigating a potential system or screen freeze during an electrostatic discharge.

27 Claims, 10 Drawing Sheets

(56) References Cited

U.S. PATENT DOCUMENTS

| | | |
|---|---|---|
| 5,717,558 A | 2/1998 | Lynn et al. |
| 5,767,647 A | 6/1998 | Akiyama et al. |
| 5,894,423 A | 4/1999 | Ling et al. |
| 5,951,836 A | 9/1999 | McAleer et al. |
| 6,169,944 B1 | 1/2001 | Hayasaka |
| 6,241,862 B1 | 6/2001 | McAleer et al. |
| 6,284,125 B1 | 9/2001 | Hodges et al. |
| 6,413,410 B1 | 7/2002 | Hodges et al. |
| 6,733,655 B1 | 5/2004 | Davies et al. |
| 6,781,522 B2 | 8/2004 | Sleva et al. |
| 7,042,428 B2 * | 5/2006 | Park ............... 345/87 |
| 7,079,369 B2 | 7/2006 | Hulfachor et al. |
| 7,112,265 B1 | 9/2006 | McAleer et al. |
| 7,181,350 B2 | 2/2007 | Oberding et al. |
| 7,241,265 B2 | 7/2007 | Cummings et al. |
| 7,250,105 B1 | 7/2007 | Davies et al. |
| 7,404,796 B2 | 7/2008 | Ginsberg |
| 2002/0091796 A1 | 7/2002 | Higginson et al. |
| 2004/0133455 A1 | 7/2004 | McMahon |
| 2004/0174489 A1 | 9/2004 | Su |
| 2004/0179315 A1 | 9/2004 | Iwasaki |
| 2004/0185817 A1 | 9/2004 | Park |
| 2004/0239660 A1 * | 12/2004 | Tsuda et al. ............ 345/204 |
| 2005/0267780 A1 | 12/2005 | Ray et al. |
| 2005/0277164 A1 | 12/2005 | Drucker et al. |
| 2006/0036134 A1 | 2/2006 | Tarassenko et al. |
| 2006/0229502 A1 | 10/2006 | Pollock et al. |
| 2006/0245131 A1 | 11/2006 | Ramey et al. |
| 2007/0084734 A1 * | 4/2007 | Roberts et al. .......... 205/792 |
| 2007/0255114 A1 | 11/2007 | Ackermann et al. |
| 2008/0108884 A1 * | 5/2008 | Kiani ................. 600/301 |
| 2008/0117346 A1 | 5/2008 | Jepsen |
| 2008/0194934 A1 | 8/2008 | Ray et al. |
| 2009/0108013 A1 | 4/2009 | Van Der Velde et al. |

FOREIGN PATENT DOCUMENTS

| | | |
|---|---|---|
| EP | 1302926 B1 | 8/2005 |
| EP | 1717924 A2 | 11/2006 |
| EP | 1783486 A1 | 5/2007 |
| EP | 1889570 A2 | 2/2008 |
| JP | 09-145665 | 6/1997 |
| JP | H10-303991 | 11/1998 |
| JP | 2000-194304 | 7/2000 |
| JP | 2001-92417 | 4/2001 |
| JP | 2003-185992 | 7/2003 |
| JP | 2007114197 A | 5/2007 |
| JP | 2008-525813 | 7/2008 |
| WO | WO 02099762 A2 | 12/2002 |
| WO | WO 2005054846 A1 | 6/2005 |
| WO | WO 2005087091 A2 | 9/2005 |
| WO | WO 2008/040984 | 4/2008 |
| WO | WO 2008061552 A1 | 5/2008 |
| WO | WO 2009151651 A | 12/2009 |

OTHER PUBLICATIONS

Japanese Patent Application No. 2011-533806, Japanese Notice of Reasons for Rejection dated Feb. 26, 2013, 2 pages, Japanese Patent Office.

Chinese Patent Application No. 200980153644.1, Chinese Office Action dated Jan. 4, 2013, 11 pages, State Intellectual Property Office, P.R. China.

Search Report issued in related Chinese Patent Application No. 200980153644.1, dated Dec. 18, 2012, 2 pages.

Search Report issued in related Chinese Patent Application No. 200980153644.1, dated Aug. 20, 2013, 2 pages.

Second Office Action issued in related Chinese Patent Application No. 200980153644.1, dated Aug. 29, 2013, 11 pages.

Third Office Action issued in related Chinese Patent Application No. 200980153644.1, dated Mar. 3, 2014, 10 pages.

Examination Report issued in related European Patent Application No. 09744431.9, dated Dec. 12, 2013, 5 pages.

Patent Examination Report issued in related Australian Patent Application No. 2009309458, Jun. 4, 2014, 3 pages.

Fourth Office Action issued in related Chinese Patent Application No. 200980153644.1, issued Oct. 15, 2014, 22 pages.

* cited by examiner

METHODS AND DEVICES FOR MITIGATING ESD EVENTS

CROSS-REFERENCE

This application claims priority under 35 USC§§365 or 371 from International Application number PCT/GB2009/002502, filed Oct. 21, 2009, which claims priority benefits to U.S. Provisional Patent Application Ser. No. 61/108,839 filed on Oct. 27, 2008, all of the prior applications are incorporated herein by reference.

BACKGROUND

Under certain circumstances, electrostatic discharge (ESD) can cause problems with medical devices. Typical handling of a medical device can generate ESD voltages of 25 kilovolts or more. While each discharge can be extremely short in duration, such high voltages can cause disruptions to electronic devices such as loss of memory, device reset, or even physical damage that results in fusing or rupture of device components. For example, a sufficiently strong ESD event can cause a display on a medical device to freeze, which gives the appearance that the device has locked up. The display on a medical device can be particularly vulnerable because it is an electronic component that is often close to the source of the injected ESD. Accordingly, applicants believe that there is a need to better mitigate the risk of ESD events at a display of a medical device or at other sensitive electronic components.

SUMMARY OF THE DISCLOSURE

A method of operating a test meter is provided that can be achieved by: displaying a screen image on a display of the test meter; saving the screen image to a memory; monitoring electrical surges at the display; detecting a magnitude of an electrical surge that is not within a predetermined range; and refreshing the display to have the saved screen image when the magnitude of the electrical surge is not within the predetermined range.

A method of operating a docking station that can be achieved by coupling a test meter to the docking station; displaying a screen image on a display of the docking station; saving the screen image to a memory; monitoring electrical surges at the display; detecting a magnitude of an electrical surge that is not within a predetermined range; and refreshing the display to have the saved screen image when the magnitude of the electrical surge is not within the predetermined range.

A docking station is provided that includes a mating interface; a display, a memory; a comparator; and a microprocessor. The mating interface is configured to be coupled to a test meter. The display is disposed on the docking station and configured to show a screen image. The memory in the docking station is configured to save a screen image. The comparator circuit in the docking station is configured to monitor electrical surges at the display. The comparator circuit is electrically connected to the display and a microprocessor. The microprocessor is configured to refresh the display to the saved screen image when a magnitude of an electrical surge is not within a predetermined range so that the display does not freeze during an ESD event.

A test meter is provided that includes a display, memory, comparator, and microprocessor. The display is disposed on the test meter and configured to show a screen image. The memory in the test meter is configured to save a screen image. The comparator circuit in the test meter is configured to monitor electrical surges at the display, the comparator circuit being electrically connected to the display and a microprocessor. The microprocessor is configured to refresh the display to the saved screen image when a magnitude of an electrical surge is not within a predetermined range so that the display does not freeze during an ESD event.

BRIEF DESCRIPTION OF THE DRAWINGS

The accompanying drawings, which are incorporated herein and constitute part of this specification, illustrate presently preferred embodiments of the invention, and, together with the general description given above and the detailed description given below, serve to explain features of the invention, in which.

DETAILED DESCRIPTION OF ILLUSTRATIVE EMBODIMENTS

The following detailed description should be read with reference to the drawings, in which like elements in different drawings are identically numbered. The drawings, which are not necessarily to scale, depict selected exemplary embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. In addition, as used herein, the terms "patient," "host," "user," and "subject" refer to any human or animal subject and are not intended to limit the systems or methods to human use, although use of the subject invention in a human patient represents a preferred embodiment.

Medical devices, such as a glucose meter, can collect data over time that reflects a user's physiological condition. Once data is collected, a user or health care provider may want to transfer the data to a server so that it can be analyzed. A docking station, that incorporates a modem, can be used to interface with the glucose meter and then transfer the data to a server. The use of a docking station to transfer data can be an automatic process where a user does not have to manually enter the data or provide an adapter cable to interface to the glucose meter.

Figure 1:
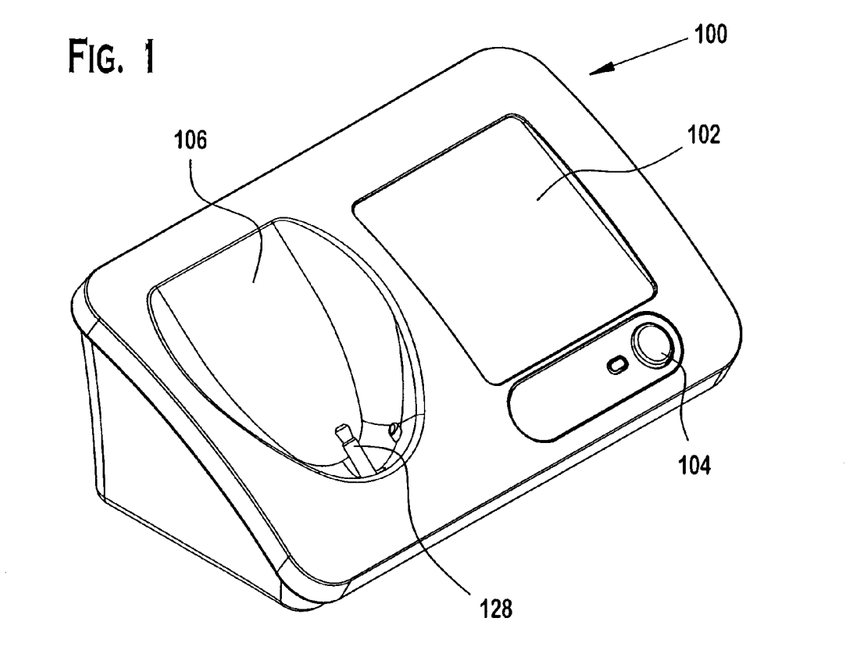
FIG. 1 illustrate a top perspective view of a docking station.
Figure 2:
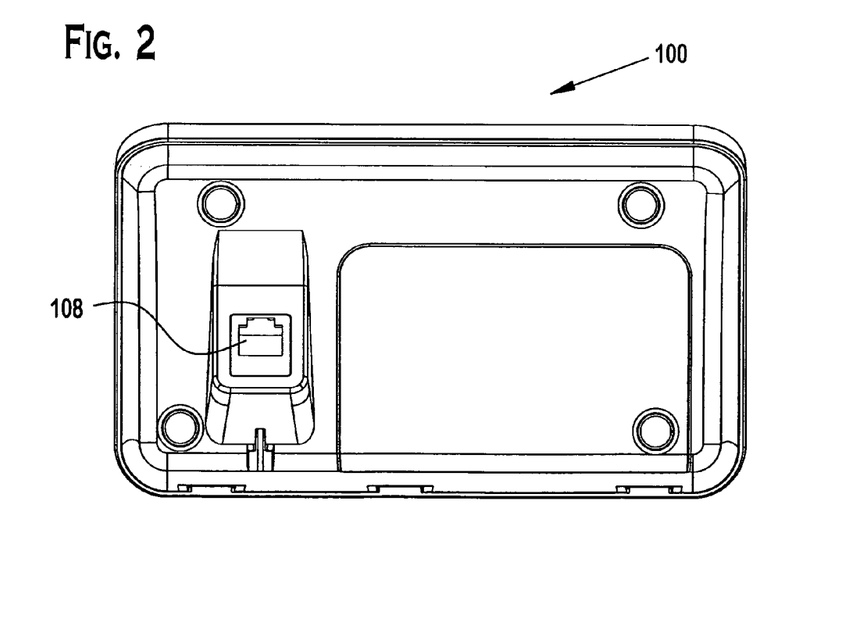
FIG. 2 illustrate a bottom view of the docking station.
Figure 4:
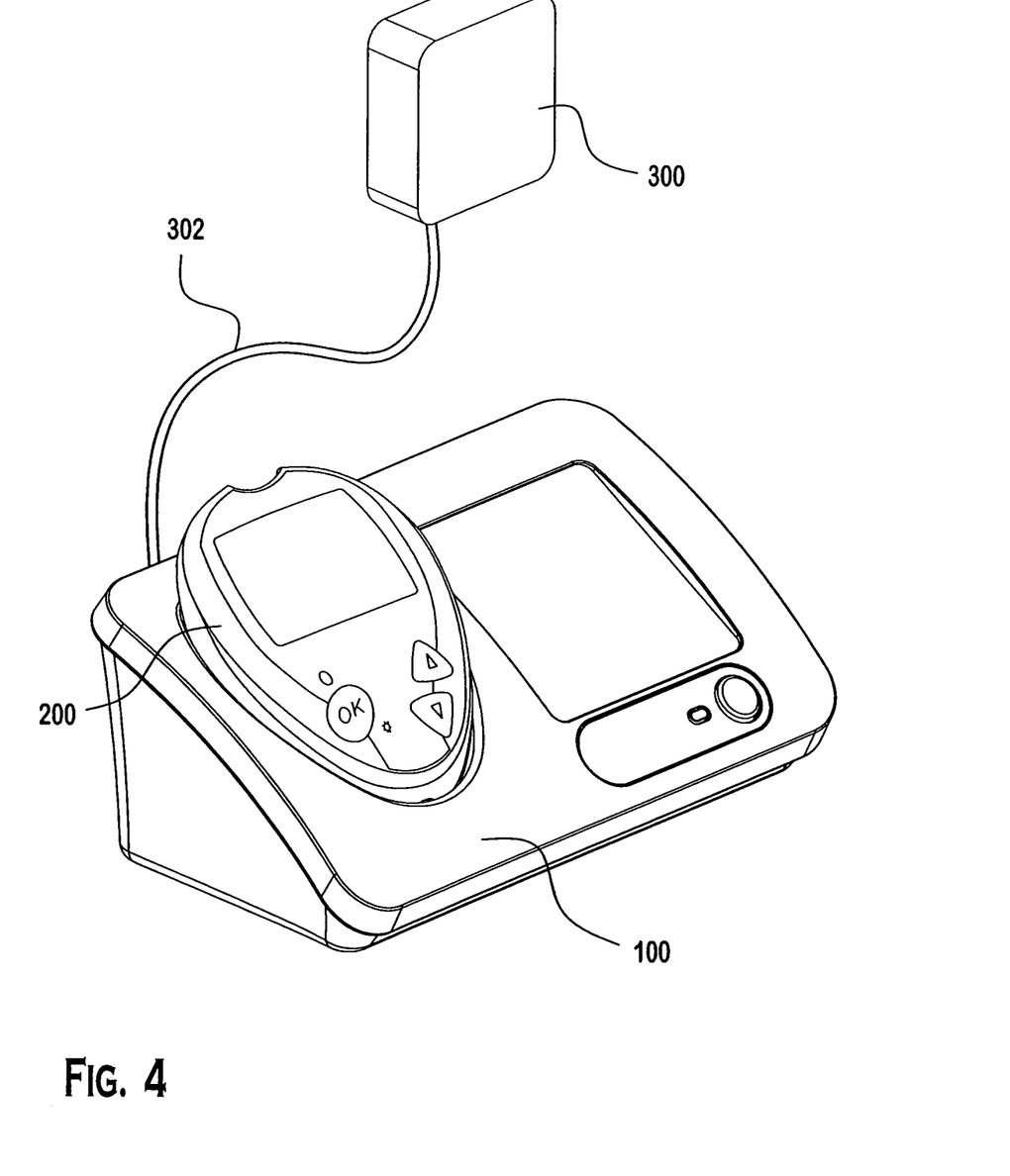
FIG. 4 illustrate a top perspective view of the docking station coupled to the test meter and to a server.

FIGS. 1, 2, and 4 illustrate a docking station 100 that includes a first display 102, a first user interface button 104, a mating interface 106, and a modem port 108. First display 102 may be a liquid crystal display or a bistable display configured to show a screen image. Examples of a screen image may include a user interface for instructing a user how to upload data from a medical device and a status indicator for showing the percent of data already downloaded. Mating interface 106 can be configured to contact a data port of a medical device so that data can be transferred to docking station 100. Modem port 108 can be configured to interface to a telephone line 302 so that data can be transferred to a server 300, as shown in FIGS. 2 and 4. Note that docking station 100 may also be referred to as a cradle.

Figure 3:
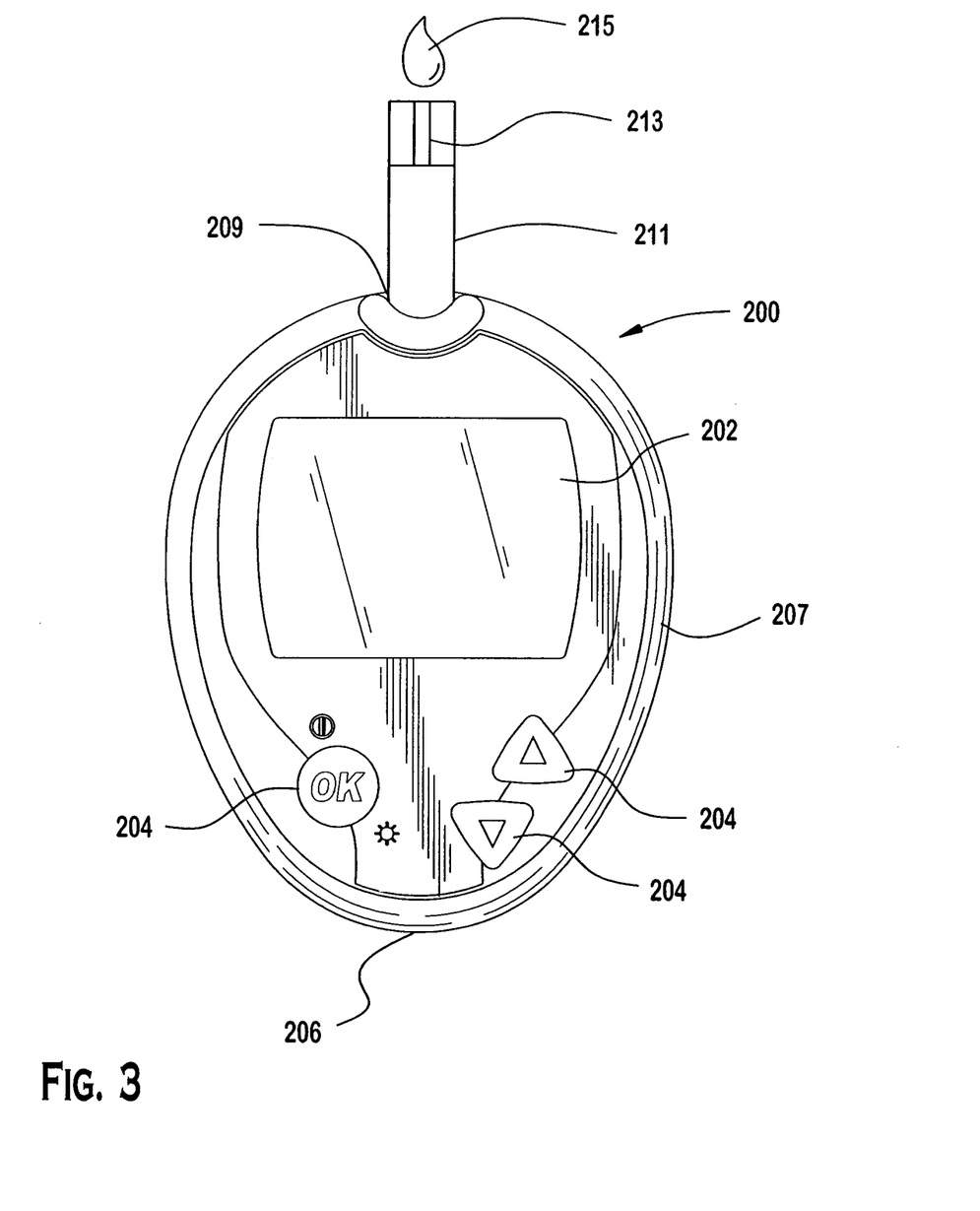
FIG. 3 illustrate a top view of a test meter that is connected to a test strip.

FIG. 3 illustrates another medical device, which in this case is a test meter 200. An example of a test meter may be the commercially available OneTouch® Ultra® 2 glucose meter from LifeScan Inc. (Milpitas, Calif.). Examples of test meters can be found in U.S. Pre-Grant Publications Nos. 2007/0084734; and 2007/0087397, which are hereby incorporated by reference herein. Test meter 200 includes a second display 202, second user interface buttons 204, a strip port connector 209, a data port 206, and a housing 207. Similar to docking station 100, second display 202 may be a liquid crystal display or a bistable display configured to show a screen image. An example of a screen image may include a glucose concentration, a date and time, an error message, and a user interface for instructing a user how to perform a test.

Strip port connector 209 can be configured to mate with a test strip 211, as shown in FIG. 3. An example of a test strip may be an electrochemical test strip, which can be a commercially available OneTouch® Ultra® glucose test strip from LifeScan Inc. (Milpitas, Calif.). Examples of test strips can be found in U.S. Pat. Nos. 5,708,247; 5,951,836; 6,241,862; 6,284,125; 6,413,410; 6,733,655; 7,112,265; 7,241,265; and 7,250,105, which are hereby incorporated by reference herein. Once test strip 211 is properly mated with test meter 100, a blood sample 215 can be dosed into a sample-receiving chamber 213. In an embodiment, test strip 211 can include an enzyme that can selectively and quantitatively transform an analyte into another chemical form. For example, test strip 211 can include ferricyanide and glucose oxidase so that glucose can be physically transformed into an oxidized form.

Mating interface 106 of docking station 100 can be configured to mate with data port 206 of test meter 200, as indicated in FIG. 4. Mating interface 106 can include a recessed area that conforms to the shape of housing 207. Mating interface 106 can also include electrical contacts 128, as illustrated in FIG. 2, that connect to data port 206. Data port 206 can be in the form of a female stereo jack receptor configured to interface with male electrical contacts of mating interface 106. Note that mating interface 106 should not be limited to an electrical interface and that other data transfer conduits could be employed such as RF, microwave, inductive, and IR.

Figure 5:
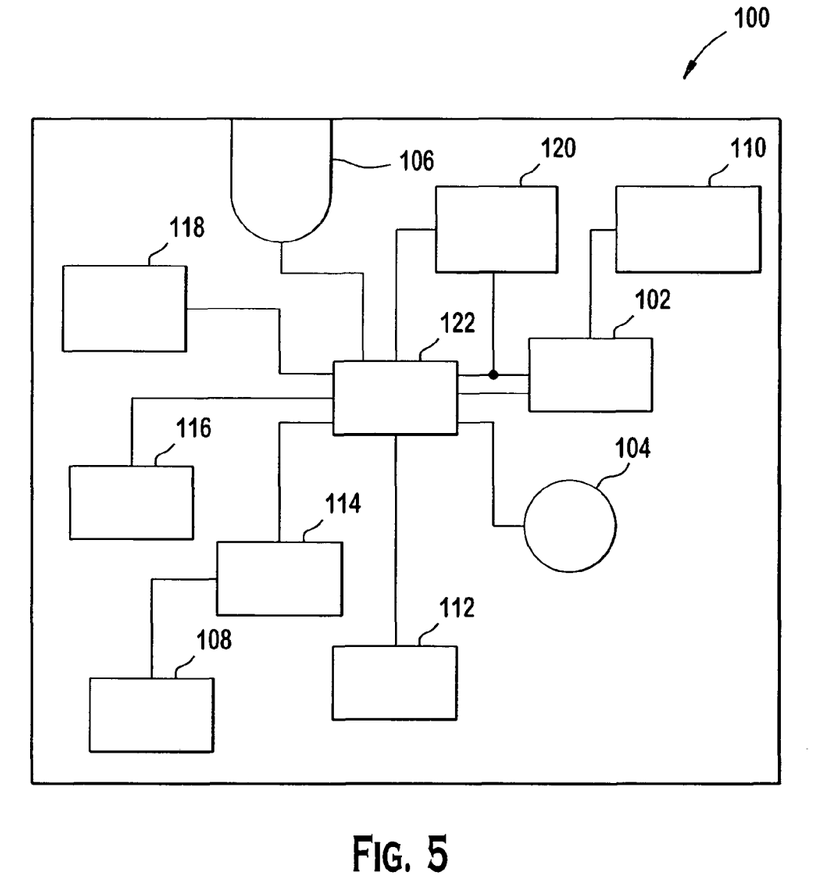
FIG. 5 illustrates a schematic of the functional components of the docking station.

FIG. 5 illustrates exemplary a schematic of the functional components of docking station 100, which further includes a first capacitance circuit 110, a first memory 112, a modem 114, a first clock 116, a first power supply 118, a first comparator circuit 120, and a first microprocessor 122. Docking station 100 should not be limited to using modem 114 for transmitting data in that other electronic components can be used such as RF, microwave, IR, and cellular phone networks. Capacitance circuit 110 can include a plurality of capacitors located relatively close to first display 102 to help dampen an electrical surge or ESD strike.

Figure 6:
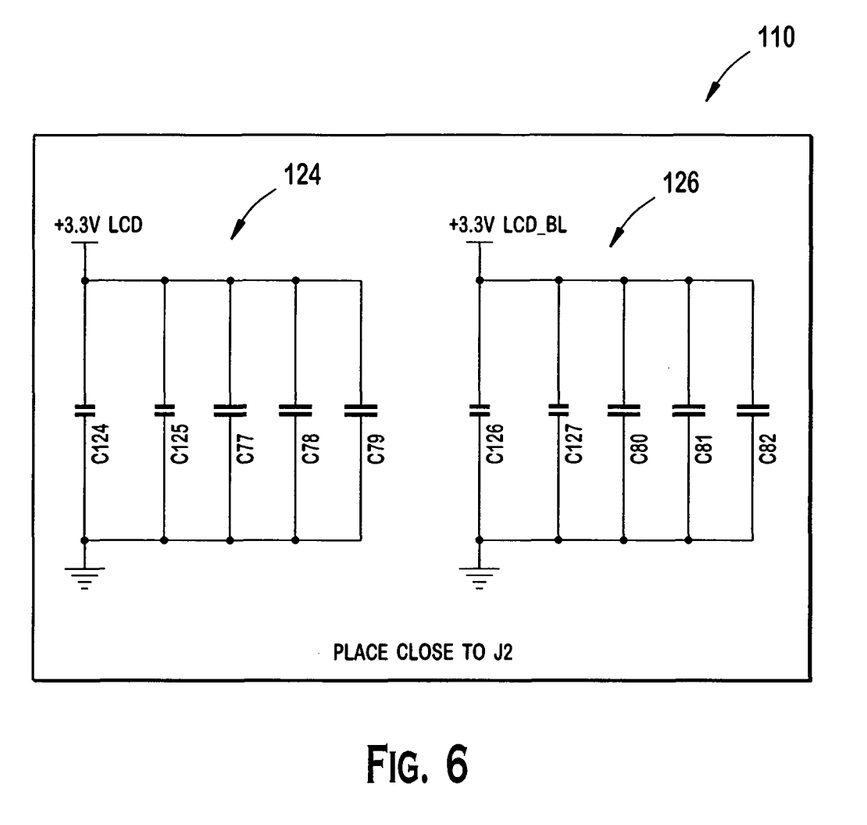
FIG. 6 illustrates an exemplary embodiment of a capacitance circuit for absorbing ESD.

An exemplary embodiment of first capacitance circuit 110 is shown in FIG. 6. First capacitance circuit 110 includes a first display capacitance circuit 124 and a backlight capacitance circuit 126. First display 102 may include a backlight for helping a user to read first display 102 more easily in low light conditions. First display capacitance circuit 124 includes five capacitors (C124, C125, C77, C78, and C79) in parallel where one end of the circuit is connected to first power supply 118 and the other end is connected to ground. Backlight capacitance circuit 126 also includes five capacitors in parallel (C126, C127, C80, C81, and C82) where one end of the circuit is connected to a power supply for the backlight and the other end is connected to ground. The capacitance values for the capacitors in first display capacitance circuit 124 and backlight capacitance circuit 126 may range from about 0.1 microfarads to about 22 microfarads.

Although capacitance circuit 110 helps mitigate the risk of damage from ESD, a sufficiently large ESD strike can still cause problems with first display 102 such as, for example, causing first display 102 to freeze. Docking station 100 can be more susceptible to an ESD strike than other medical devices because it is often connected to a grounded telephone line 302. ESD can tend to travel through the electronics of docking station 100 when telephone line 302 is connected to an earth ground. If a docking station is configured to transfer data wirelessly to a server or is disconnected from a grounded telephone line, then ESD can be directed to a negative terminal of the battery instead of the electronics of the docking station. However, applicants believe that docking station 100, as described herein, is typically attached to an earth ground creating a need for more effective ESD protection.

An ESD strike can cause the voltage applied to first display 102 to either increase or decrease. For example, ESD can attenuate the applied voltage from first power supply 118 to first display 102. Alternatively, under certain circumstances, ESD can cause the applied voltage from first power supply 118 to increase. In an embodiment, a voltage boost circuit can be used to apply an elevated voltage to first display 103 that is higher than the voltage from first power supply 118. When the applied voltage to first display is not within a specified range, first display 102 can exhibit a frozen state such as, for example, all pixels turned off, all pixels turned on, a random mix of some pixels turned off and other pixels turned on, or all pixels remain static from the last screen image. Under certain circumstances, a frozen first display 102 may be fixed by removing and re-inserting the battery in docking station 100 or by turning the power off and then on. However, manipulating batteries or a power switch is not desirable because it takes time, is annoying to the user, and could cause confusion.

In an embodiment, docking station 100 can be designed for simplicity such that it does not have a power on switch or replaceable batteries. A user would not need to turn the power on because docking station 100 can turn on automatically when test meter 200 is mated with mating interface 106. Docking station 100 can turn off automatically after a predetermined amount of time has elapsed where there is no activity. Also, a user would not need to replace the batteries if they were designed to last the lifetime of the device. In such a situation, the battery door compartment could be sealed shut. Because this embodiment would not be able to recover from an ESD strike by removing and re-inserting the batteries or by turning the power of and then on, applicants believe that there is a need for a more robust ESD mechanism.

First memory 112 can be configured to save a screen image that is shown on first display 102, as illustrated in FIG. 5. In an embodiment, first memory 112 can be integrated with first microprocessor 122. Modem 114 can be configured to transfer data from docking station 100 through telephone line 302 to server 300. First power supply 118 can be configured to provide power to docking station 100 either by an AC power source or a battery. First display 102 can include a voltage boost circuit that is configured to increase a voltage from first power supply 118. The voltage boost circuit can be integrated with first display 102.

First comparator circuit 120 can be configured to monitor electrical surges at first display 102, as illustrated in FIG. 5. In an embodiment, first comparator circuit 120 can be electrically connected to first display 102 and first microprocessor 122. More particularly, first comparator circuit 120 can be electrically connected to the voltage boost circuit of first display 102 and first microprocessor 122.

Figure 7A:
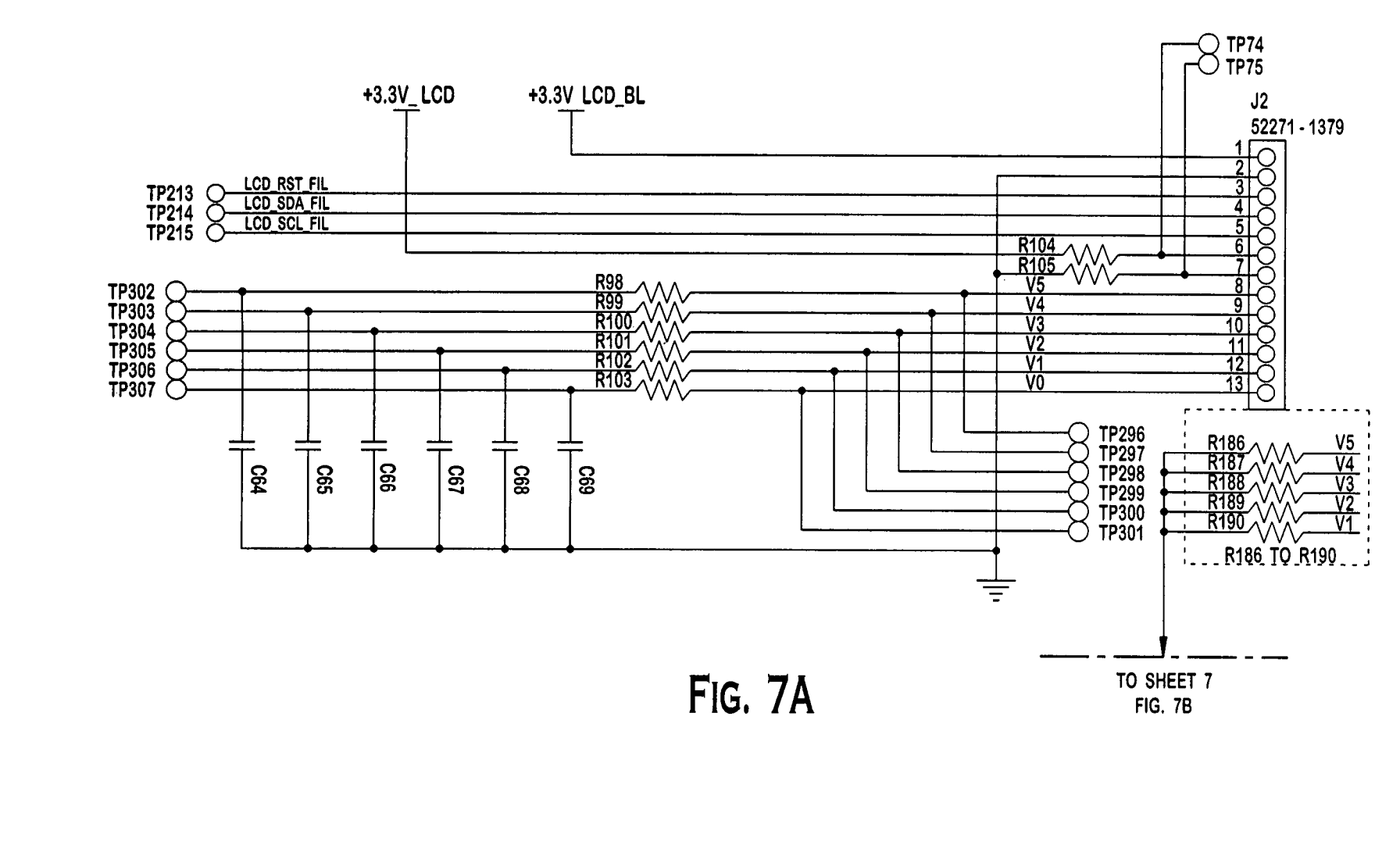
FIGS. 7A and 7B illustrates an exemplary embodiment of a circuit that includes a comparator circuit for monitoring electrical surges.
Figure 7B:
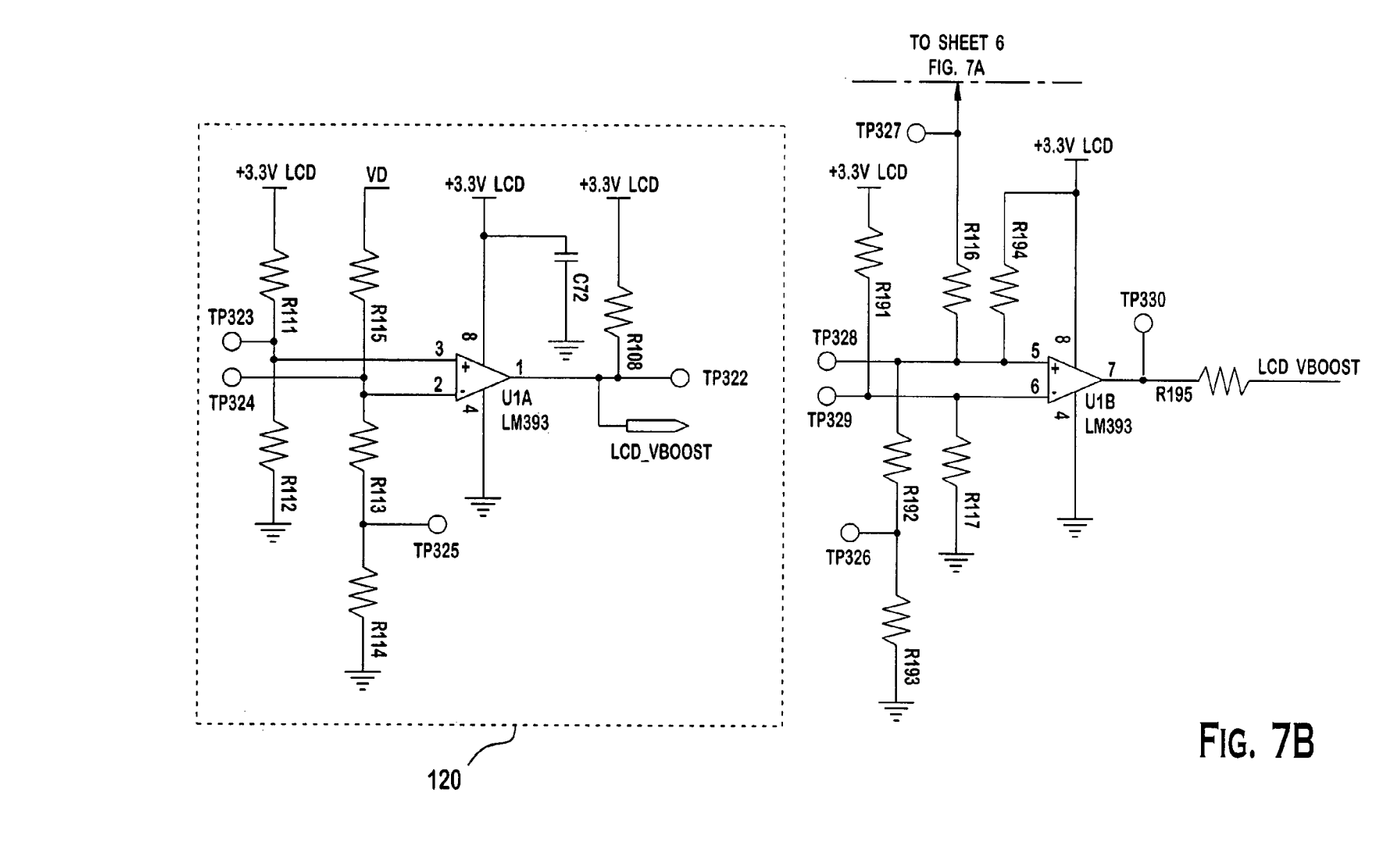

An exemplary embodiment of a circuit that includes first comparator circuit 120 is shown in FIGS. 7A and 7B. Pins 8 to 13 are the various voltage boosts for first display 102, which are represented as V5, V4, V3, V2, V1, and V0, respectively, in FIG. 7A. First comparator circuit 120 is in the form of an operational amplifier labeled as U1A on FIG. 7B. A positive input 3 receives a fixed voltage at about 1.65 Volts. A negative input 2 receives a scaled down voltage of V0, which is about 1.8 Volts to about 2 Volts. In this case, V0 is scaled down by about 0.167x. The voltage V0 represents a voltage applied to first display 102 at pin 13 and ranges from about 11 Volts to about 12 Volts. V0 is a voltage generated by a voltage boost circuit that is part of first display 102. First comparator circuit 120 may monitor the voltage boost having a highest voltage magnitude, which in this case is V0, so that a decrease in voltage will be relatively easy to detect. Thus, if ESD causes the voltage boost at pin 13 to turn off, a drop in voltage at V0 will have largest change in magnitude compared to the other voltage boosts (V1, V2, V3, V4, and V5). In another embodiment, more than one voltage boost may be monitored for ESD events such as, for example, using an operational amplifier U1B in FIG. 7B.

An output 1 is configured to provide a high logic state when the voltage V0 significantly increases or decreases from a specified voltage range as a result of an electrical surge or ESD. If the voltage V0 remains within the specified voltage range, output 1 will provide a low logic state. Output 1 is connected to an interrupt of first microprocessor 122. More particularly, output 1 is connected to pin 17, which is labeled as LCD_Vboost in FIG. 8B. First comparator 120 does not have to be limited to the electronic circuit illustrated in FIG. 7B and could be substituted with other electronic circuits such as a circuit including an A/D converter and another microprocessor for monitoring the applied voltage to first display 102.

Figure 8A:
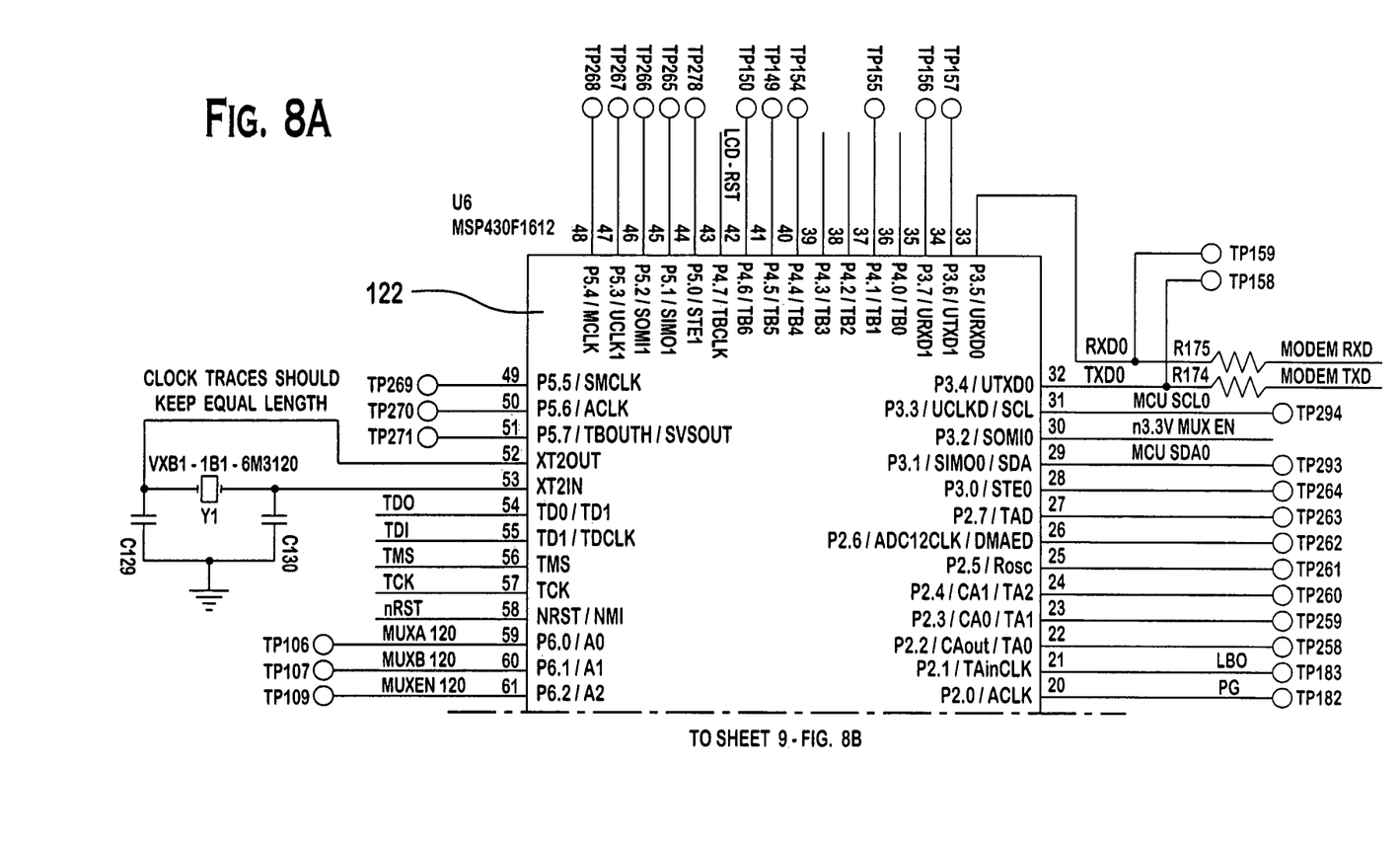
FIGS. 8A and 8B illustrate an exemplary embodiment of a microprocessor.
Figure 8B:
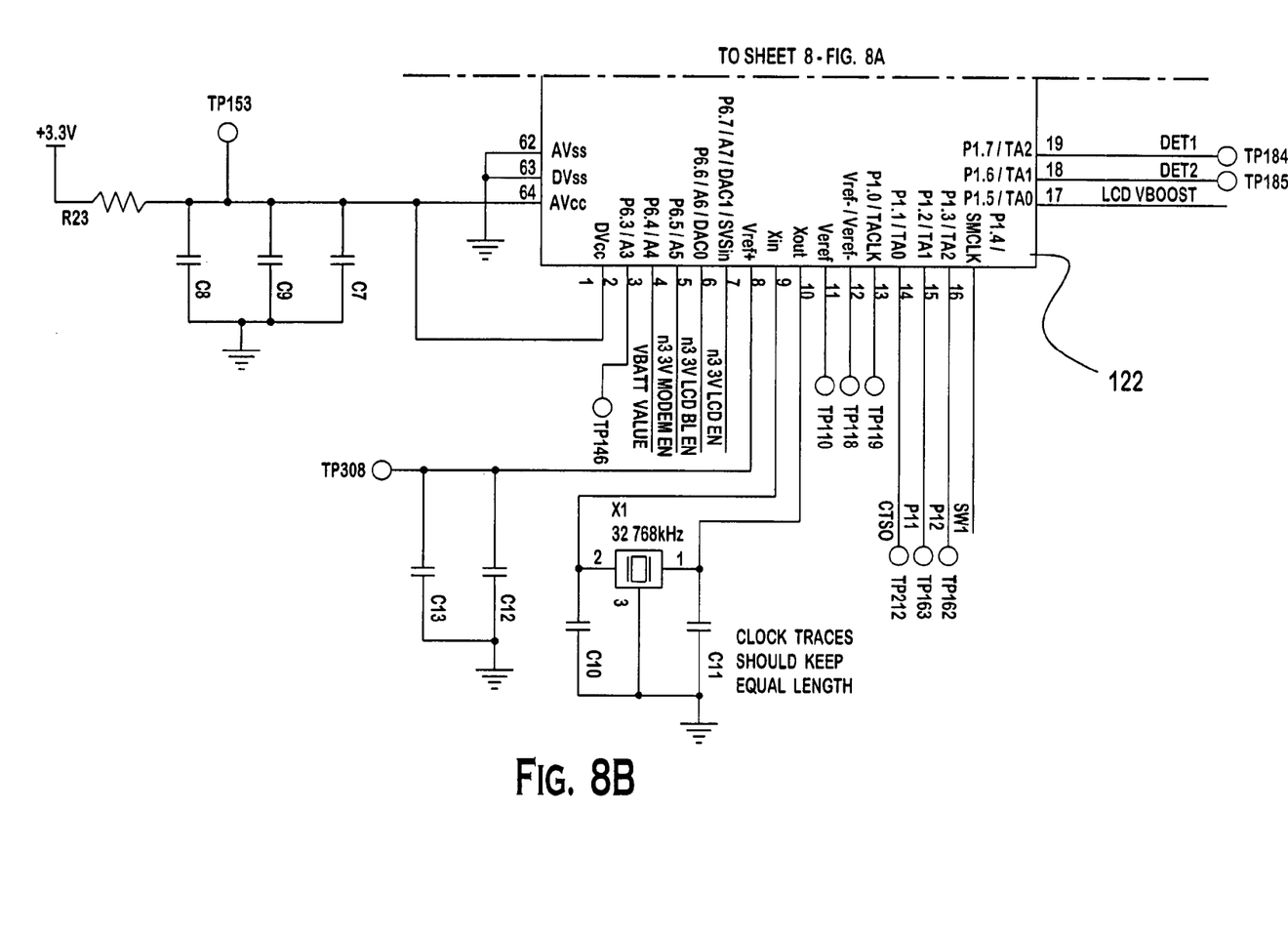
Figure 9:
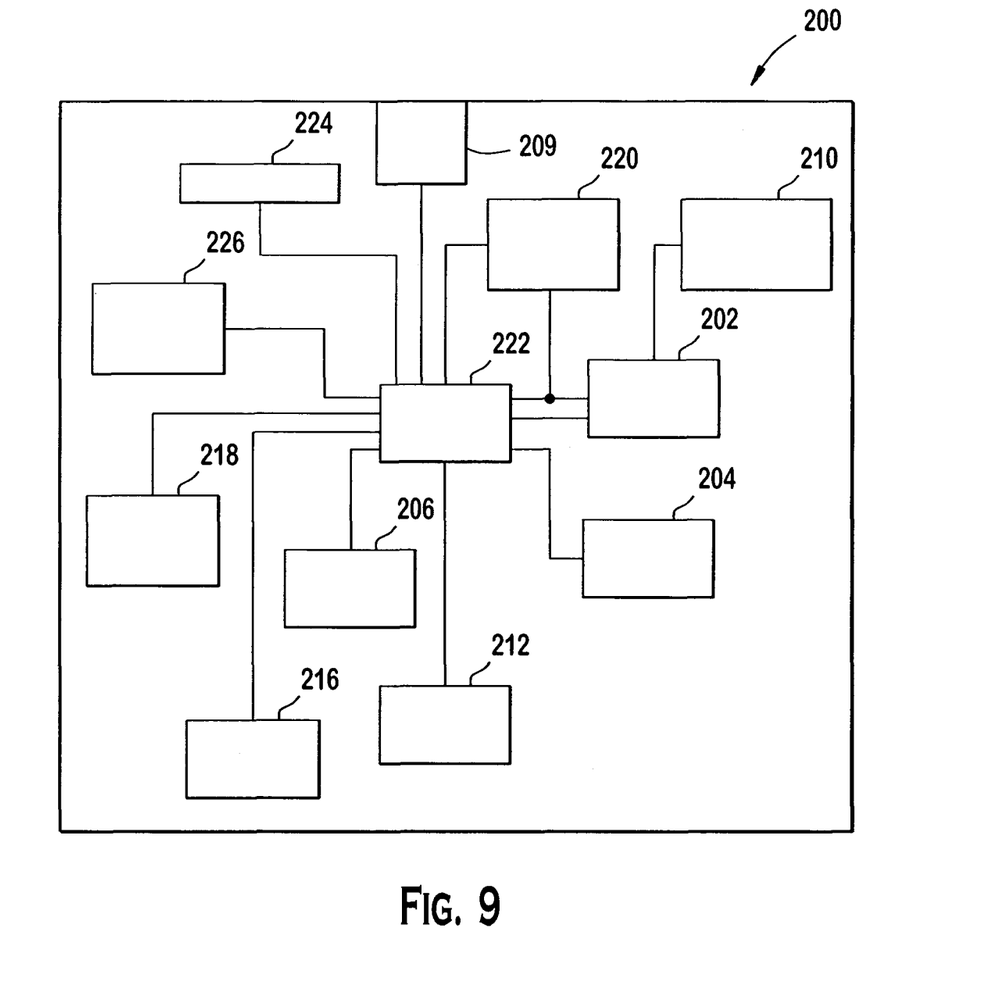
FIG. 9 illustrates a schematic of the functional components of the test meter.

First microprocessor 122 can be configured to re-set and/or refresh first display 102 to a saved screen image when a magnitude of an electrical surge is not within predetermined range. First microprocessor 122 can also be configured to run firmware or software in first memory 112, which controls the data download process from test meter 200 and the upload process to server 300 via modem 114. First microprocessor 122 can be electrically connected to mating interface 106, first display 102, first memory 112, and first comparator circuit 120 so that first display 102 does not freeze during an ESD event. An exemplary embodiment of first microprocessor 122 is shown in FIGS. 8A and 8B. First microprocessor 122 includes a pin 17 that is connected to output 1 of first comparator circuit 120 and a pin 43 that is connected to a re-set pin of first display 102. Upon receipt of a high logic state from output 1 to pin 17, first microprocessor can re-set first display 102 and then refresh first display 102 with the previously saved screen image The following will describe a test meter 200 that implements an ESD mitigation mechanism, which uses electronic components similar to docking station 100. FIG. 9 illustrates a schematic of the functional components of test meter 200, which further includes a second capacitance circuit 210, a second memory 212, a second clock 216, a second power supply 218, a second comparator circuit 220, a potentiostat 224, a current measurement circuit 226, and a second microprocessor 222.

Second capacitance circuit 210 can be similar to first capacitance circuit 110. Second memory 212 can be configured to save a screen image that is shown on second display 202. Second comparator circuit 220 can be configured to monitor electrical surges at second display 202. In an embodiment, second comparator circuit 220 can be electrically connected to second display 202 and second microprocessor 222. Second comparator circuit 220 can be similar to first comparator circuit 120.

Second display 202 can include a voltage boost circuit that is configured to increase a voltage from second power supply 218. The voltage boost circuit can be integrated with second display 202.

Potentiostat 224 can include electronic circuitry for applying a test voltage between at least two electrodes. Current measurement circuit 226 can include a circuit configured to quantitate a magnitude of a test current resulting from the applied test voltage. An example of current measurement circuit 226 may include a current-to-voltage converter.

Second microprocessor 222 can be configured to re-set and/or refresh second display 202 to a saved screen image when a magnitude of an electrical surge is not within a predetermined range. Second microprocessor 222 can be electrically connected to second display 202, second memory 212, and second comparator circuit 220 so that second display 202 does not freeze during an ESD event. More specifically, second microprocessor 222 may be electrically connected to a voltage boost of second display 202.

Now that docking station 100 and test meter 200 have been described, the following will describe a method of operating docking station 100 and also for operating test meter 200. A method of operating docking station 100 includes coupling test meter 200 to docking station 100. Data port 206 of test meter 200 can be connected to mating interface 106 of docking station 100. Housing 207 can conform to a recess portion of mating interface 106 when coupling test meter 200 to docking station 100.

Once test meter 200 is coupled to docking station 100, docking station 100 can then power on from a low power sleep mode, download data from test meter 200, process the data, and then transmit the processed data to server 300. If docking station 100 does not successfully transmit the data to server 300, docking station 100 can automatically retry. Processing the data may include collecting the glucose concentrations, the units of measure, meal flags, comments, meter serial number, control solution yes/no, docking station serial number, and docking station battery level. A physician, nurse, diabetes educator, or health care provider can then review the data transmitted to server 300 to assess the general health of the user and possibly make a therapeutic recommendation. Before transmitting the data to server 300, docking station 100 can filter the data such as, for example, by determining which portion of the data has already been sent and sending only the unsent portion. Docking station battery level can be transmitted so that a doctor, nurse, diabetes educator, or health care provider can advise a user to change the battery if the power is low or to use another docking station having a fresh battery. Docking station 100 can encrypt data using a data key based on the serial number of test meter 200 before it is sent to server 300.

First clock 116 of docking station 100 can send the date and time to server 300. If the date and time differs from that on server 300, the date and time of first clock 116 can then be corrected. Docking station 100 can determine when test meter 200 has been removed and then provide a message to a user on first display 102 if such removal was before all of the data was transmitted.

First display 102 can display a screen image to provide feedback to a user. For example, the screen image can include messages from the user's health care provider based on past glucose readings transmitted to server 300. First display 102 can have a backlight that comes on when docking station 100 is in use, but will switch off when there is a period of inactivity. A screen image on first display 102 can be saved to first memory 112. Every time the screen image changes, the new screen image can be saved to first memory 112.

Docking station 100 can monitor for electrical surges at first display 102. More specifically, docking station 100 can monitor for electrical surges at a voltage boost of first display 102. First comparator circuit 120, which is electrically connected to first display 102 and first microprocessor 122, can monitor for electrical surges by detecting a decrease or increase in applied voltage. Applicant has discovered that the applied voltage of the voltage boost tends to turn off after a sufficiently strong ESD event. However, under certain circumstances, ESD events can increase the applied voltage at the voltage boost. If an electrical surge is detected in that the voltage applied to first display 102 is not within a predetermined range, then first display 102 should be refreshed to the saved screen image. Once first comparator circuit 120 detects an electrical surge that is not within a predetermined range, it can trigger an interrupt of first microprocessor 122 so that first display 102 is re-initialized and then refreshed to the saved screen image.

The predetermined range can include a lower limit and an upper limit. In an embodiment, the lower limit can be less than about 10 Volts and the upper limit can be infinity. The lower limit can be based on the reference voltage of 1.65 Volts that is fed into the positive input 3, as shown in FIG. 7B. Thus, the lower limit could be 1.65 Volts divided by a 0.167 scaling factor that equals 9.9 Volts. For the situation in which ESD events do not cause the voltage boost to increase the applied voltage, the upper limit can be set to infinity.

In another embodiment where ESD can cause the voltage boost to increase or decrease the applied voltage, the lower limit can be less than about 10 Volts and the upper limit can range from about 12 volts to about 13 volts. The upper limit can be set to be an upper specification value of the voltage boost circuitry or alternatively can be set to be the upper specification value plus an incremental value that accounts for routine short term variation in the applied voltage. For the situation where a voltage boost has a normal operating characteristic ranging from about 11 volts to about 12 Volts, the upper limit can be set at about 12 Volts or greater.

Applicants have discovered that the use of first comparator circuit 120 for detecting electrical surges and the use of first memory for saving each screen image helped to reduce the likelihood of first display 102 from becoming frozen. In addition, the use of first capacitance circuit 110 further reduced the risk of problems occurring from ESD.

Before coupling docking station 100 to test meter 200, test meter 200 can be tested with one or more test strips. For a test, test strip 211 can be mated with test meter 200. Next, blood sample 215 can be applied to test strip 211. Test meter 200 can then measure a glucose concentration of blood sample 215. The process of measuring the glucose concentration can include a physical transformation of glucose into an oxidized form.

In an embodiment, a method of operating a test meter 200 includes displaying a screen image on second display 202. A screen image on second display 202 can be saved to second memory 212. Every time the screen image changes, the new screen image can be saved to second memory 212.

Test meter 200 can monitor for electrical surges at second display 202. More specifically, test meter 200 can monitor for electrical surges at a voltage boost of second display 202. Second comparator circuit 220, which is electrically connected to second display 202 and second microprocessor 222, can monitor for electrical surges by detecting a decrease or increase in applied voltage. Applicant has discovered that the applied voltage of the voltage boost tends to turn off after a sufficiently strong ESD event. However, under certain circumstances, ESD events can increase the applied voltage at the voltage boost. If an electrical surge is detected in that the voltage applied to second display 202 is not within a predetermined range, then second display 202 should be refreshed to the saved screen image. Once second comparator circuit 220 detects an electrical surge that is not within a predetermined range, it can trigger an interrupt of second microprocessor 222 so that second display 202 is re-initialized and then refreshed to the saved screen image. The predetermined range for test meter 200 can be about the same as docking station 100.

Under certain conditions, an ESD strike can be detected at the display, but the ESD does not disrupt the function of the microprocessor. Thus, when an ESD strike is detected at the display, the microprocessor is capable of refreshing the saved screen image and continuing the test. Even though the display could have been momentarily frozen due to ESD, a user would not realize it because the microprocessor is able to re-set and immediately refresh the display with a previously saved image, and continue with the test.

For example, test meter 200 can flash some icons on second display 202 showing a test strip, a finger, and a drop of blood indicating that a user can apply blood to the test strip. In a first scenario where an ESD mitigating mechanism is not deployed, a sufficiently strong ESD event can cause the display to freeze. Since the icons prompting a user to dose the test strip may still be shown, a user may then dose the test strip with blood. The test meter will then perform the test, but the glucose concentration will not be shown because the display is frozen. Because the microprocessor can still be functioning, a proper glucose concentration would be calculated, but cannot be shown because of the frozen display. In order unfreeze the screen, the user may have to remove and re-insert the batteries or turn the meter off and then on so that the microprocessor can be re-set and, in turn, re-fresh the display. In the first scenario, the test strip will likely be wasted because the user cannot determine the glucose concentration output.

In a second scenario where an ESD mitigating method described herein is used, a test can be performed seamlessly even though a relatively strong ESD event occurs at the display. Here, a sufficiently strong ESD can cause the display to freeze. For example, the icons prompting a user to dose the test strip will remain static on the display. However, the comparator circuit will recognize the electrical surge and automatically re-initialize the display allowing it to refresh based on subsequent microprocessor commands. The display can be refreshed to show the previously saved icons prompting a user to dose the test strip without the user realizing that an ESD event had occurred. Because the display is not frozen, it can respond to subsequent microprocessor commands to perform the test and show the calculated glucose concentration. Thus, even though a relatively strong ESD event temporarily froze the display, a valid glucose concentration can be shown as a screen image without the annoyance of wasting a test strip.

While preferred embodiments of the present invention have been shown and described herein, it will be obvious to those skilled in the art that such embodiments are provided by way of example only. For example, the invention can be applied not only to docking stations and glucose meters, but can also be applied to any electronic device that needs a power supply and that can be re-set such as insulin infusion pump, continuous glucose monitoring system and the like. Numerous variations, changes, and substitutions will now occur to those skilled in the art without departing from the invention. Various alternatives to the embodiments of the invention described herein may be employed in practicing the invention. It is intended that the following claims define the scope of the invention and that methods and structures within the scope of these claims and their equivalents be covered thereby.

What is claimed is:

1. A method of operating a test meter, the method comprising:
    displaying a screen image on a display of the test meter;
    saving the screen image to a memory;
    monitoring electrical surges at the display;
    detecting a magnitude of an electrical surge that is not within a predetermined range; and
    refreshing the display to have the saved screen image when the magnitude of the electrical surge is not within the predetermined range.

2. The method of claim 1, in which the display comprises a liquid crystal display.

3. The method of claim 1, in which the electrical surge comprises an electrostatic discharge.

4. The method of claim 1, in which the electrical surge attenuates a voltage applied to the display.

5. The method of claim 1, in which the electrical surge increases a voltage applied to the display.

6. The method of claim 1, in which the refreshing comprises re-initializing the display.

7. The method of claim 1, in which the monitoring comprises a comparator circuit.

8. The method of claim 7, in which the comparator circuit triggers a microprocessor to refresh the display.

9. The method of claim 1, in which the monitoring comprises a circuit that includes a microprocessor connected to an analog-to-digital converter, the circuit configured to monitor electrical surges.

10. The method of claim 7, in which the comparator circuit is electrically connected to the display and a microprocessor of the test meter.

11. The method of claim 10, in which the comparator circuit is electrically connected to a voltage boost of the display and a microprocessor of the test meter.

12. The method of claim 11, in which the predetermined range comprises a lower limit and an upper limit, the lower limit being based on a reference voltage that is fed into a positive input of an operational amplifier of the comparator circuit and the upper is limit is infinity.

13. The method of claim 11, in which the predetermined range comprises a lower limit and an upper limit, the lower limit being based on a reference voltage that is fed into a positive input of an operational amplifier of the comparator circuit and the upper is limit is based on an upper specification value of the voltage boost.

14. The method of claim 12, in which the lower limit is less than about 10 Volts.

15. The method of claim 12 or claim 13, in which the lower limit is less than about 10 Volts and the upper limit is greater than about 12 Volts.

16. The method of claim 1 further comprising:
    coupling a test strip to the test meter;
    applying a sample to the test strip; and
    measuring a concentration of the sample.

17. The method of claim 16, in which the measuring comprises a physical transformation of glucose into an oxidized form.

18. A method of operating a docking station, the method comprising:
    coupling a test meter to the docking station;
    displaying a screen image on a display of the docking station;
    saving the screen image to a memory;
    monitoring electrical surges at the display;
    detecting a magnitude of an electrical surge that is not within a predetermined range; and
    refreshing the display to have the saved screen image when the magnitude of the electrical surge is not within the predetermined range.

19. The method of claim 18, in which the display comprises a liquid crystal display.

20. The method of claim 18, in which the electrical surge comprises an electrostatic discharge.

21. The method of claim 18, in which the electrical surge attenuates a voltage applied to the display.

22. The method of claim 18, in which the electrical surge increases a voltage applied to the display.

23. The method of claim 18, in which the refreshing comprises re-initializing the display.

24. The method of claim 18, in which the monitoring comprises a comparator circuit.

25. The method of claim 18, in which the comparator circuit triggers a microprocessor to refresh the display.

26. The method of claim 18, in which the monitoring comprises a circuit that includes a microprocessor connected to an analog-to-digital converter, the circuit configured to monitor electrical surges.

27. The method of claim 24, in which the comparator circuit is electrically connected to the display and a microprocessor of the docking station.

* * * * *